United States Patent
Fraga da Silva et al.

(10) Patent No.: US 10,300,279 B2
(45) Date of Patent: May 28, 2019

(54) SYSTEMS AND METHODS FOR TREATING SEXUAL DISORDERS USING ELECTRO-STIMULATION

(71) Applicant: ECOLE POLYTECHNIQUE FEDERALE DE LAUSANNE (EPFL), Lausanne (CH)

(72) Inventors: Rodrigo Araujo Fraga da Silva, Lausanne (CH); Nikolaos Stergiopulos, Preverenges (CH)

(73) Assignee: Ecole Polytechnique Federale De Lausanne (EPFL), Lausanne (CH)

(*) Notice: Subject to any disclaimer, the term of this patent is extended or adjusted under 35 U.S.C. 154(b) by 64 days.

(21) Appl. No.: 15/793,781

(22) Filed: Oct. 25, 2017

(65) Prior Publication Data
US 2018/0043164 A1    Feb. 15, 2018

Related U.S. Application Data

(63) Continuation of application No. 14/880,903, filed on Oct. 12, 2015, now Pat. No. 9,821,163.
(Continued)

(51) Int. Cl.
*A61N 1/36* (2006.01)
*A61N 1/05* (2006.01)
*A61N 1/372* (2006.01)

(52) U.S. Cl.
CPC ....... *A61N 1/36107* (2013.01); *A61N 1/0558* (2013.01); *A61N 1/36007* (2013.01);
(Continued)

(58) Field of Classification Search
CPC .............. A61N 1/36107; A61N 1/0558; A61N 1/36007; A61N 1/36185; A61N 1/37247; A61N 1/37264
(Continued)

(56) References Cited

U.S. PATENT DOCUMENTS 3,941,136 A    3/1976  Bucalo
4,585,005 A *  4/1986  Lue .................... A61N 1/36007
                                              607/39
(Continued)

FOREIGN PATENT DOCUMENTS

WO    WO-96/39932 A1    12/1996
WO    WO-03/018113 A1    3/2003
(Continued)

OTHER PUBLICATIONS

Alsaid, et al., Coexistence of adrenergic and cholinergic nerves in the inferior hypogastric plexus: anatomical and immunohistochemical study with 3D reconstruction in human male fetus, J. Anat., 214(5):645-654 (2009).
(Continued)

*Primary Examiner* — Carl H Layno
*Assistant Examiner* — Erin M Piateski
(74) *Attorney, Agent, or Firm* — Foley & Lardner LLP; Christopher C. Bolten; Nicola A. Pisano

(57) ABSTRACT

Systems and methods are provided for treating a sexual disorder such as erectile dysfunction (ED) or female sexual arousal disorder (FSAD). An electrical stimulation system may include an implantable stimulation unit, an external patient controller, and an external physician controller. The implantable stimulation unit has an array of electrodes disposed on one or more flexible substrates configured to conform to a patient's anatomy at the pelvic plexus. Post-implantation, the physician controller may direct the stimulation unit to stimulate with select electrode(s) of the array to determine which electrode configuration provides optimal sexual arousal. The patient controller may be used to cause the stimulation unit to stimulate using the optimal electrode configuration at desired times.

18 Claims, 9 Drawing Sheets

Related U.S. Application Data

(60) Provisional application No. 62/063,301, filed on Oct. 13, 2014.

(52) U.S. Cl.
CPC ..... *A61N 1/36185* (2013.01); *A61N 1/37247* (2013.01); *A61N 1/37264* (2013.01)

(58) Field of Classification Search
USPC .......................................................... 607/39
See application file for complete search history.

(56) References Cited

U.S. PATENT DOCUMENTS

| | | | |
|---|---|---|---|
| 5,215,088 | A | 6/1993 | Normann et al. |
| 5,454,840 | A | 10/1995 | Krakovsky et al. |
| 5,938,584 | A | 8/1999 | Ardito et al. |
| 6,128,536 | A | 10/2000 | Noack et al. |
| 6,169,924 | B1 | 1/2001 | Meloy et al. |
| 6,505,074 | B2 | 1/2003 | Boveja et al. |
| 6,650,943 | B1 | 11/2003 | Whitehurst et al. |
| 6,885,895 | B1 | 4/2005 | Whitehurst et al. |
| 7,006,870 | B1 | 2/2006 | Whitehurst et al. |
| 7,096,070 | B1 | 8/2006 | Jenkins et al. |
| 7,328,068 | B2 | 2/2008 | Spinelli et al. |
| 7,328,069 | B2 | 2/2008 | Gerber |
| 7,330,762 | B2 | 2/2008 | Boveja et al. |
| 7,338,522 | B2 | 3/2008 | Greenberg et al. |
| 7,369,894 | B2 | 5/2008 | Gerber |
| 7,427,280 | B2 | 9/2008 | Gerber |
| 7,734,355 | B2 | 6/2010 | Cohen et al. |
| 7,865,243 | B1 | 1/2011 | Whitehurst et al. |
| 8,630,711 | B1 | 1/2014 | Wark et al. |
| 2003/0004553 | A1 | 1/2003 | Grill et al. |
| 2003/0236557 | A1* | 12/2003 | Whitehurst .......... A61N 1/0556 607/39 |
| 2004/0049240 | A1 | 3/2004 | Gerber et al. |
| 2004/0073268 | A1 | 4/2004 | Zappala |
| 2005/0010260 | A1 | 1/2005 | Gerber |
| 2005/0131484 | A1 | 6/2005 | Boveja et al. |
| 2005/0283202 | A1 | 12/2005 | Gellman |
| 2006/0129028 | A1 | 6/2006 | Krakousky |
| 2006/0135862 | A1 | 6/2006 | Tootle et al. |
| 2007/0027514 | A1* | 2/2007 | Gerber .................. A61N 1/05 607/116 |
| 2007/0078493 | A1 | 4/2007 | Gerber |
| 2007/0255333 | A1* | 11/2007 | Giftakis ............. A61N 1/36007 607/39 |
| 2008/0065167 | A1* | 3/2008 | Boggs, II ................. A61N 1/05 607/39 |
| 2008/0091244 | A1 | 4/2008 | Richardson |
| 2008/0140168 | A1* | 6/2008 | Walter ................. A61N 1/0553 607/117 |
| 2013/0123684 | A1 | 5/2013 | Giuffrida et al. |
| 2014/0277266 | A1 | 9/2014 | Khalil et al. |
| 2014/0288616 | A1 | 9/2014 | Rawat et al. |
| 2014/0304773 | A1 | 10/2014 | Woods et al. |

FOREIGN PATENT DOCUMENTS

| | | |
|---|---|---|
| WO | WO-2009/023543 A2 | 2/2009 |
| WO | WO-2013/011474 A1 | 1/2013 |

OTHER PUBLICATIONS

Burnett, et al., Intraoperative Assessment of an Implantable Electrode Array for Cavernous Nerve Stimulation, J. Sex Med., 5(8):1949-1954 (2008).

Burnett, et al., Neuromodulatory therapy to improve erectile function recovery outcomes after pelvic surgery, J. Urol., 176(3):882-887 (2006).

Costello, et al., Immunohistochemical study of the cavernous nerves in the periprostatic region, BJU Int., 107(8):1210-1215 (2011).

Dean, et al., Physiology of Penile Erection and Pathophysiology of Erectile Dysfunction, Urol. Clin. North Am. 32(4):379-95 (2005).

Eardley, et al., Pharmacotherapy for erectile dysfunction, J. Sex. Med., 7:524-40 (2010).

Harding, et al., Comparison of a needle-free high-pressure injection system with needle-tipped injection of intracavernosal alprostadil for erectile dysfunction, Int. J. Impot. Res., 14(6):498-501 (2002).

International Search Report and Written Opinion dated Jan. 20, 2016 in Int'l PCT Patent Application Serial No. PCT/IB2015/057809.

Klotz, et al., Early experience with intraoperative cavernous nerve stimulation with penile tumescence monitoring to improve nerve sparing during radical prostatectomy, Urology, 52(4):537-542 (1998).

Klotz, et al., Intraoperative cavernous nerve stimulation during nerve sparing radical prostatectomy: how and when?, Curr. Opin. Urol., 10(3):239-43 (2000).

Leungwattanakij, et al., Intracavernosal injection and intraurethral therapy for erectile dysfunction, Urol. Clin. North Am. 28(2):343-54 (2001).

Lue, et al., Electrostimulation and penile erection, Urol. Int., 40(1):60-4 (1985).

Lue, et al., Intraoperative Electrostimulation of the Cavernous Nerve: Technique, Results and Limitations, The Journal of Urology, 154:1426-1428 (1995).

Penson, et al., 5-Year Urinary and Sexual Outcomes After Radical Prostatectomy: Results From the Prostate Cancer Outcomes Study, J. Urol., 179 (5 Suppl): S40-4 (2008).

Ponnusamy, et al., Nerve mapping for prostatectomies: novel technologies under development, J. Endourol. 26(7):769-77 (2012).

Rotella, Phosphodiesterase 5 inhibitors: current status and potential applications, Nat. Rev. Drug Discov., 1(9):674-82 (2002).

Sadeghi-Nejad, Penile prosthesis surgery: a review of prosthetic devices and associated complications, J. Sex. Med., 4(4):1520 (2007).

Shafik, A., Extrapelvic cavernous nerve stimulation in erectile dysfunction. Human study. Andrologia, 28(3):151-156 (1996).

Shafik, et al., Magnetic stimulation of the cavernous nerve for the treatment of erectile dysfunction in humans, Int. J. Impot. Res., 12(3):137-41 (2000).

Shafik, et al., Percutaneous Perineal Electrostimulation Induces Erection: Clinical Significance in Patients With Spinal Cord Injury and Erectile Dysfunction, J. Spinal. Cord. Med., 31(1):40-3 (2008).

Takenaka, et al., Variation in course of cavernous nerve with special reference to details of topographic relationships near prostatic apex: histologic study using male cadavers, Urology, 65(1):136-142 (2005).

* cited by examiner

SYSTEMS AND METHODS FOR TREATING SEXUAL DISORDERS USING ELECTRO-STIMULATION

CROSS-REFERENCE TO RELATED APPLICATIONS

This application is a continuation of U.S. patent application Ser. No. 14/880,903, filed Oct. 12, 2015, now U.S. Pat. No. 9,821,163, issued Nov. 21, 2017, which claims the benefit of priority of U.S. Provisional Patent Application No. 62/063,301, filed Oct. 13, 2014, the entire contents of each of which are incorporated herein by reference.

FIELD OF THE INVENTION

The present disclosure relates to implantable electrical stimulation systems and methods for treating and preventing sexual disorders such as erectile dysfunction, female sexual arousal disorders, erectile dysfunction following prostatectomy surgery, and erectile dysfunction associated with spinal cord injury.

BACKGROUND OF THE INVENTION

A sexual disorder (e.g., sexual dysfunction, sexual malfunction) is a complication experienced by an individual, male or female, or a couple during any stage of normal sexual activity, including erection, physical pleasure, desire, preference, arousal, or orgasm. Sexual dysfunctions generally have a profound impact on an individual's quality of life. The most prevalent sexual disorders are erectile dysfunction (ED) and female sexual arousal disorders (FSAD).

Penile erection is a coordinated neurocardiovascular response. See, Dean R C and Lue T F, *Physiology of penile erection and pathophysiology of erectile dysfunction*, Urol Clin North Am. 2005 November; 32(4):379-95. In the flaccid state, the penile smooth muscles are tonically contracted, allowing only a small amount of blood flow for nutritional purposes. Penile erection occurs when sexual stimulation triggers release of neurotransmitters, mainly nitric oxide, from the cavernous nerve terminals. The neurotransmitters cause relaxation of the smooth muscle cells in cavernosal arterioles and sinuses, resulting in increased blood flow into the penis. This causes the cavernous sinuses to fill with blood and expand against the tunica albuginea, partially occluding the venous outflow, thus resulting in an erection.

ED is a multi-causal disease with diversified etiologies, and may be psychogenic, vasculogenic, hormonal, or neurogenic. However, studies show that the neurogenic and vasculogenic causes are the most prevalent. In general, the major mechanisms responsible for ED are a failure in the neuronal response (e.g., prostatectomy, cystectomy, abdominoperineal resection, spinal cord injury, or diabetes) or an increase in the tone and/or contractility of the smooth muscle within the corpus cavernosum and penile arteries (e.g., hypertension, atherosclerosis and diabetes). See, Sadeghi-Nej ad H., *Penile prosthesis surgery: a review of prosthetic devices and associated complications*, Sex Med. 2007 March; 4(2):296-309.

Prostatectomy is known to cause severe ED. This essential surgical procedure, generally for treatment of prostate cancer, often leads to ED due to the inevitable disruption of the neural pathway for erectile function. These intimal nerves are located around the prostate, and may be damaged during the surgery. Currently, surgeons attempt to perform a nerve-sparing surgery; however, in the actual scenario, an astounding 70% of patients undergoing prostatectomy will develop ED. See, Penson D F, McLerran D, Feng Z, Li L, Albertsen P C, Gilliland F D, Hamilton A, Hoffman R M, Stephenson R A, Potosky A L, Stanford J L., *5-year urinary and sexual outcomes after radical prostatectomy: results from the Prostate Cancer Outcomes Study*, J Urol. 2008 May; 179(5 Suppl): S40-4.

Pharmacological treatments are currently available for ED. These drugs (e.g., sildenafil, Viagra®; tadalafil, Cialis® or vardenafil, Levitra®) are efficient for the majority of ED patients; however, they show low effectiveness for ED resulting from prostatectomy or others causes associated with failure in the neuronal response. Such drugs act by potentiating the actions of the neurotransmitter nitric oxide, by inhibiting the enzyme phosphodiesterase type 5 [PDE-5]. See, Rotella D P., *Phosphodiesterase 5 inhibitors: current status and potential applications*, Nat Rev Drug Discov. 2002 September; 1(9):674-82. PDE-5 is an enzyme responsible for breaking down the intracellular second messenger cGMP generated by NO stimulus. cGMP is involved in the regulation of some protein-dependent kinases, which relax smooth muscle cells and facilitate erection. Thus, patients with disruption of the erectile neural response do not respond well to such medications. One alternative for these patients is intrapenial injections of vasodilators, which produce direct erection, independent of the neural pathway. See, Leungwattanakij S, Flynn V Jr, Hellstrom W J, *Intracavernosal injection and intraurethral therapy for erectile dysfunction*, Urol Clin North Am. 2001 May; 28(2):343-54 and Harding L M, Adeniyi A, Everson R, Barker S, Ralph D J, Baranowski A P, *Comparison of a needle free high-pressure injection system with needle-tipped injection of intracavernosal alprostadil for erectile dysfunction*, Int J Impot Res. 2002 December; 14(6):498-501. Alprostadil (Prostaglandin E1, PGE1) is the most common vasodilator used for ED. See, Harding and Eardley I, Donatucci C, Corbin J, El-Meliegy A, Hatzimouratidis K, McVary K, Munarriz R, Lee S W, *Pharmacotherapy for erectile dysfunction*, J Sex Med. 2010 January; 7(1 Pt 2):524-40. The vasodilator may be injected into the corpus cavernosum with a needle and is effective in over 80% of patients. See, Harding. Common side effects of intrapenial injection are penile pain, bleeding, hematoma, priapism, and penile fibrosis, which can lead to permanent ED. See, Leungwattanakij.

Another option for these patients is penile implants, which consist of a pair of malleable or inflatable rods surgically implanted within the erection chambers of the penis. See, Sadeghi-Nejad. There are different types of penile prosthesis (rigid, semi-rigid, or inflatable) and all them normally require an irreversible and destructive surgery with risk of intra and post-operative complications. Such prosthesis frequently require surgery revision. Nevertheless, prosthesis implantation is a common procedure due to the lack of better treatment options. Thus, there is a clear need for better therapeutic strategy for the treatment of ED resulting from failure of the neural pathway, such as post-prostatectomy ED, providing a painless, safe, easier, non-traumatic and more effective alternative.

Numerous studies have shown that cavernous nerve stimulation can induce and maintain erection in animals and men. See, Lue T F, Schmidt R A, Tanagho E A, *Electrostimulation and penile erection*, Urol Int. 1985; 40(1):60-4; Shafik A, Shafik A A, Shafik I A, El Sibai O., *Percutaneous perineal electrostimulation induces erection: clinical significance in patients with spinal cord injury and erectile dysfunction*, J Spinal Cord Med. 2008; 31(1):40-3; and Shafik A, el-Sibai O, Shafik A A, *Magnetic stimulation of the cavernous nerve for the treatment of erectile dysfunction in humans*, Int J Impot Res. 2000 June; 12(3):137-41. Since then, electroneurostimulation for erectile response has been considered an option for patients undergoing prostatectomy. However, no one has developed an implantable neuroelectrostimulation system specifically for ED that reached satisfactory results in the clinic. The barrier for the development of such technology is the complex anatomy of the human cavernous nerve. See, Klotz L., *Intraoperative cavernous nerve stimulation during nerve sparing radical prostatectomy: how and when*? Curr Opin Urol. 2000 May; 10(3):239-43 and Ponnusamy K, Sorger J M, Mohr C., *Nerve mapping for prostatectomies: novel technologies under development*, J Endourol. 2012 July; 26(7):769-77. Locating the optimal site for electroneurostimulation is difficult, since the human cavernous nerve travels from the pelvic-plexus to the penis through a complex anastomosis. Moreover, there is a significant anatomic variability in the location of the cavernous nerve. Each patient's anatomy, disease stage, and cancer location are unique. The pelvic-plexus is a diaphanous veil with microscopic nerves and the cavernous nerve is not disposed uniformly in every man. Therefore, these barriers make the identification of the cavernosal nerve segments for selective stimulation extremely difficult.

In previously proposed systems, localization and identification of the cavernosal nerve is conducted during implantation surgery. For example, U.S. Pat. No. 4,585,005 to Lue requires previous identification and isolation of the cavernous nerves. U.S. Pat. No. 7,328,068 to Spinelli describes a method for stimulation of the penile neural pathway in which precise positioning of the implant is required to provide optimal stimulation. In Spinelli, a neurophysiological monitoring assessment could be used as method to locate the optimal stimulation site before implantation. U.S. Pat. No. 7,330,762 to Boveja discloses systems for electroneurostimulation of the cavernosal nerve, including different types of electrodes, such as spiral electrodes, cuff electrodes, steroid eluting electrodes, wrap-around electrodes and hydrogel electrodes. Again, identification of the optimal site for stimulation is required before implantation. U.S. Pat. No. 7,865,243 to Whitehurst describes systems and methods for stimulation of the cavernosal nerve; however, the anatomical identification of the course of the pudendal nerve and/or other nerves to be stimulated must be located before implantation.

Overall, these prior art systems and methods require identification of the optimal site of stimulation prior to implantation and tend to demand extensive operatory period, increasing the intra and post-operative risks and complications.

SUMMARY OF THE INVENTION

The present disclosure provides a neuroelectrostimulation system and methods for treating a sexual disorder, including in patients who are incapable of obtaining penile erections spontaneously (e.g., erectile dysfunction (ED) including ED associated with failure in the neuronal response such as post-prostatectomy ED) and patients suffering from female sexual arousal disorder (FSAD).

An electrical stimulation system for treatment of a sexual disorder, e.g., ED, in a patient may include an implantable stimulation unit, an external patient controller, and an external physician controller.

The implantable stimulation unit may include an array of electrodes disposed on at least one flexible substrate sized and shaped to abut at least a portion of a pelvic plexus of a patient and a programmable controller operatively coupled to the array of electrodes. The programmable controller may include a stimulation circuit, a nonvolatile memory, and a microprocessor coupled to the stimulation circuit and the nonvolatile memory. The nonvolatile memory may store an identity of an empirically determined subset of the array of electrodes and a stimulation routine used by the microprocessor to supply electrical stimulation via the stimulation circuit and the pelvic plexus to a nerve(s), e.g., at least one cavernous nerve, sufficient to cause sexual arousal, e.g., an erection. The stimulation routine may include a pulse duration, frequency, voltage, and current. Such parameters of electrical stimulation may be adjusted post-implantation by the external physician controller and, optionally, by the external patient controller. The implantable stimulation unit may have a power supply that may be rechargeable.

The external patient controller may be configured to selectably activate the implantable stimulation unit responsive to a patient input. The external physician controller may be configured to selectively activate desired subsets of the array of electrodes to determine the empirically determined subset of the array of electrodes and to cause the nonvolatile memory of the implantable stimulation unit to store the stimulation routine used by the microprocessor. The subset of the array of electrodes may include one or more electrodes within the array of electrodes.

The external physician controller may be configured to selectively activate desired subsets of the array of electrodes by causing the microprocessor to execute a scanning protocol stored in the nonvolatile memory to determine the empirically determined subset of the array of electrodes. The scanning protocol may be configured to cause the microprocessor to supply electrical stimulation via the stimulation circuit by activating varying subsets of the array of electrodes in a predetermined manner to determine the empirically determined subset of the array of electrodes and to cause the nonvolatile memory of the implantable stimulation unit to store the stimulation routine used by the microprocessor. Activating varying subsets of the array of electrodes in a predetermined manner may include activating a first subset of the array of electrodes at a first time and activating a second subset of the array of electrodes at a second time in an interpulse manner.

The implantable stimulation unit and the external patient controller communicate wirelessly. In that regard, the implantable stimulation unit may contain a first transceiver and the external patient controller may contain a second transceiver. The first and second transceivers may employ IEEE 802.11 or BLUETOOTH™ communications schemes. Wireless communications between the first and second transceivers may be encrypted. The external patient controller may be specifically designed for communication with the implantable stimulation unit or may be a smartphone, laptop, tablet, or smartwatch programmed to communicate with the implantable stimulation unit.

The implantable stimulation unit and the external physician controller communicate wirelessly and the external physician controller may contain a third transceiver. The first and third transceivers may employ IEEE 802.11 or BLUETOOTH™ communications schemes. Wireless communications between the first and third transceivers may be encrypted. The external physician controller may be specifically designed for communication with the implantable stimulation unit or may be a smartphone, laptop, tablet, or desktop computer programmed to communicate with the implantable stimulation unit.

The external physician controller may be configured to selectively activate desired subsets of the array of electrodes to determine the empirically determined subset of the array of electrodes at the time of implantation of the implantable stimulation unit and/or subsequent to implantation of the implantable stimulation unit.

The at least one flexible substrate may be configured to conform to an anatomical shape of the patients nerves such as a portion of the pelvic plexus. In one embodiment, the at least one flexible substrate comprises a first flexible substrate configured to conform to a first half of the pelvic plexus and a second flexible substrate configured to conform to a second half of the pelvic plexus. A first portion of the array of electrodes may be disposed on the first flexible substrate and a second portion of the array of electrodes may be disposed on the second flexible substrate, such that the stimulation circuit may be configured to cause one or more electrodes of the first portion and one or more electrodes of the second portion to supply electrical stimulation at the same time in a bilateral stimulation manner. The electrodes of the array of electrodes may be arranged in a plurality of rows and a plurality of columns disposed on the at least one flexible substrate, such that each electrode is individually selectable.

The implantable stimulation unit may include one or more anchors configured to maintain the at least one flexible substrate in contact with the pelvic plexus following radical prostatectomy. The anchors may be, for example, sutures or biocompatible glue.

The at least one flexible substrate may include at least one cavity configured to permit connective tissue growth in and/or through the flexible substrate(s) to anchor the flexible substrate(s) adjacent to the pelvic plexus. In addition to providing sexual arousal, the electrical stimulation may promote nerve regeneration.

Also provided herein are methods for implanting the implantable stimulation unit, methods for determining the subset of the array of electrodes for stimulation to cause optimal sexual arousal, and methods for using the system. The implantable stimulation unit may be configured for implantation using a robotic-guided surgery system. The at least one flexible substrate and the programmable controller may each be sized and shaped to be implanted through a trocar. At least one electrode of the array of electrodes may be configured to receive an electrical signal emitted by one or more external electrodes, e.g., electrodes disposed on a skin of a penis of the patient. The nonvolatile memory of the programmable controller may be configured to record and store information indicative of the received electrical signal. The information may be transmitted to external patient controller and/or external physician controller. The information may be used to determine the subset of the array of electrodes for stimulation to cause optimal sexual arousal by a user and/or automatically.

BRIEF DESCRIPTION OF THE DRAWINGS

These and other features, aspects, and advantages of the present disclosure will become apparent from the following description, appended claims, and the accompanying exemplary embodiments shown in the drawings, which are briefly described below.

FIGS. 2C through 2E are schematic representations of an exemplary implantable stimulation unit of the stimulation system of FIG. 1, wherein FIGS. 2D and 2E show the conformable nature of the implantable stimulation unit such that electrodes may be aligned adjacent to the patient's pelvic plexus.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Systems and methods described herein may be used to treat a sexual disorder such as erectile dysfunction (ED), including ED associated with failure in the neuronal response (resulting from e.g., prostatectomy, cystectomy, abdominoperineal resection, spinal cord injury, and/or diabetes) and ED associated with an increase in the tone and/or contractility of the smooth muscle within the corpus cavernosum and penile arteries (resulting from e.g., hypertension, atherosclerosis, and/or diabetes), and female sexual arousal disorder (FSAD).

Penile erection occurs when sexual stimulation triggers release of neurotransmitters, mainly nitric oxide, from the cavernous nerve terminals. Erectile dysfunction (ED) is a multicausal disease with diversified etiologies, and neurogenic ED is one of the most prevalent. Several conditions may impair the neuronal pathway for penile erection (e.g., prostatectomy, cystectomy, abdominoperineal resection, spinal cord injury, or diabetes) which lead to a malfunction or interruption of the neurotransmitters release by cavernous nerve terminals in erectile tissues.

Systems and methods described herein are expected to restore function of a denervated penis by, for example, electrostimulating the terminal extremity of the cavernosal nerve. The neuronal pathway triggering the erectile response is a parasympathetic input originated from the pelvic splanchnic nerve plexus. The pelvic splanchnic nerve plexus is comprised of branches from the second, third, and fourth sacral nerves that intertwine with the inferior hypogastric plexus, forming the network of nerves in the pelvis. The cavernous nerves are derived from the pelvic splanchnic nerves, travel along via the prostatic plexus, nearly located around the prostate, and supply parasympathetic fibers to the corpora cavernosal and corpus spongiosum of the penis. Therefore, locating the optimal site for electroneurostimulation is difficult, since the human cavernous nerve travels from the pelvic-plexus to the penis through a complex anastomosis. Moreover, there is a significant anatomic variability in the location of the cavernous nerve. Each patient's anatomy, disease stage, and/or cancer location is unique. The pelvic-plexus is a diaphanous veil with microscopic nerves and the cavernous nerves do not follow uniform localization in every man. Therefore, these barriers make identification of the cavernosal nerve segments for selective stimulation extremely difficult. Provided herein are systems and methods for overcoming these barriers.

Figure 1:
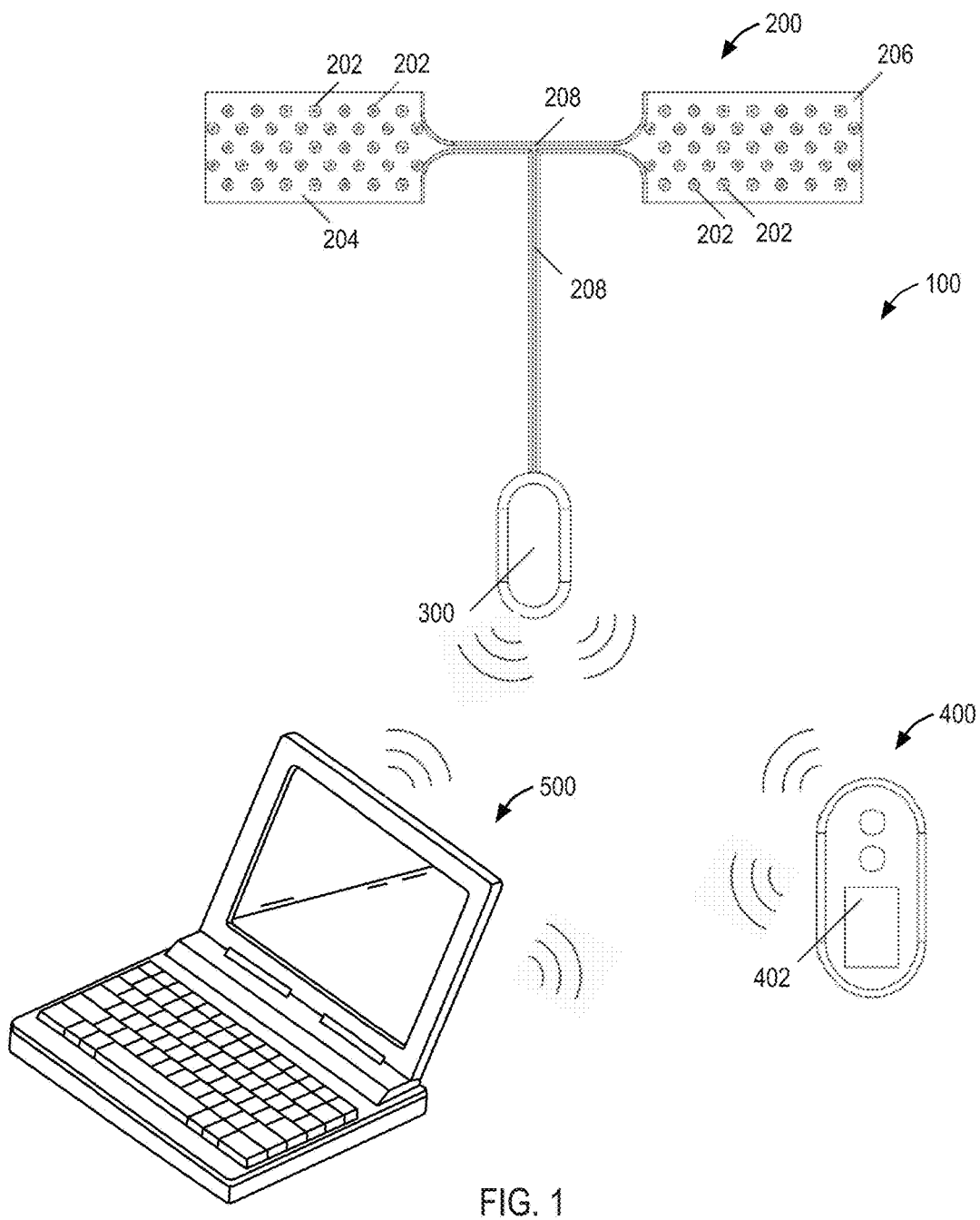
FIG. 1 is a schematic representation of an exemplary electrical stimulation system constructed in accordance with the principles of the present disclosure.

Referring to FIG. 1, an overview of an exemplary electrical stimulation system constructed in accordance with the principles of the present disclosure is provided. In FIG. 1, components of the system are not depicted to scale on either a relative or absolute basis. Electrical stimulation system 100 may include implantable stimulation unit 200 having programmable controller 300, external patient controller 400, and external physician controller 500.

Implantable stimulation unit 200 includes array 202 of electrodes disposed on at least one flexible substrate, illustratively first flexible substrate 204 and second flexible substrate 206, cable 208, and programmable controller 300. The electrodes of array 202 are configured to emit electrical energy to stimulate tissue. Preferably, the electrodes are individually selectable and one or more pairs of electrodes may be selected by a user, e.g., a physician using external physician controller 500, for stimulation. The electrodes of array 202 may be arranged uniformly and/or disposed in different spatial configuration. For example, electrodes of array 202 may be spaced apart by about 0.05 mm to about 5.0 mm, about 0.1 mm to about 4.0 mm, about 0.5 mm to about 3.0 mm, or about 0.5 mm to about 1.5 mm. Illustratively, the electrodes are arranged in a plurality of rows and a plurality of columns. The number of electrodes of array 202 may vary according to need and may be over 10, over 20, over 30, over 40, or over 50 electrodes. The electrodes may perform bipolar stimulation such that current passes from one electrode to another electrode to stimulate a nerve or a group of nerves in between the two electrodes. Electrodes of array 202 may have a tissue friendly shape configured to reduce adverse tissue reaction that may lead to fibrosis formation around the electrode. For example, the electrodes may be sized and shaped such that a convex, spherical, or flat shaped portion is exposed on the flexible substrate, avoiding sharp surfaces that may damage or irritate the tissue. The electrodes may be made of platinum, gold, or other conductible implantable material suitable for electrical stimulation of nerves.

The flexible substrate(s) having array 202 of electrodes is sized and shaped to abut at least a portion of a pelvic plexus of a patient. The flexible substrate(s) is configured to bend, e.g., to an arc shape, and may be implanted (e.g., during prostatectomy surgery) on the pelvic plexus. Preferably, the flexible substrate(s) may be conformed to an anatomical shape of a portion of the pelvic plexus and may cover part or the entire area of the pelvic plexus so that at least one of the electrodes of array 202 is in optimal contact with the cavernosal nerve. The flexible substrate(s) may comprise a structural matrix of silicone or other flexible non-conductible material, which allows adaptation and molding to the local anatomy required for better positioning and to minimize tissue reaction. The flexible substrate(s) may have a flat structure designed in a suitable shape (e.g., rectangular, squared, oval, ellipse, trapezoid) and dimensioned to better adapt to each patient's anatomy and need.

As illustrated, implantable stimulation unit 200 includes first flexible substrate 204 and second flexible substrate 206 such that implantable stimulation unit 200 resembles a T-shape. Preferably, first flexible substrate 204 is configured to conform to a first half of the pelvic plexus and second flexible substrate 206 is configured to conform to a second half of the pelvic plexus.

As illustrated, implantable stimulation unit 200 includes a first portion of array 202 of electrodes disposed on first flexible substrate 204 and a second portion of array 202 of electrodes disposed on second flexible substrate 206. The stimulation circuit may be configured to cause one or more electrodes of the first portion of array 202 of electrodes disposed on first flexible substrate 204 and one or more electrodes of the second portion of array 202 of electrodes disposed on second flexible substrate 206 to supply electrical stimulation at a same time in a bilateral stimulation manner.

Implantable stimulation unit 200 may include at least one anchor, preferably individually coupled to a flexible substrate, configured to maintain the flexible substrate in contact with the pelvic plexus. The anchor may be sutures, biocompatible matrix, or biocompatible glue. Implantable stimulation unit 200 also may be encapsulated in one or more biocompatible materials suitable for long-term implantation (e.g., titanium cage, silicone cage). In one embodiment, the flexible substrate(s) include one or more cavities in between the electrodes or at specific regions of the substrate(s) configured to permit connective tissue growth in and/or through the substrate to enhance anchoring and fixation in the pelvic cavity.

Cable 208 is configured to electrically couple the electrodes of array 202 to programmable controller 300. Cable 208 may be an insulated multi-conductor cable having an independent wire for each electrode of array 202. Cable 208 may include branches, as illustrated, permitting connection with electrodes on multiple flexible substrates.

Programmable controller 300 includes circuitry configured to store stimulation routines and to cause electrodes of array 202 to supply electrical stimulation at parameters defined by the stimulation routines. Such parameters may include pair(s) of electrodes to be used for stimulation, pulse duration, frequency of alternating current, voltage, current, period of stimulation.

Programmable controller 300 may be controlled by, and optionally powered by, external patient controller 400. External patient controller 400 has user interface 402 that permits a user, e.g., patient, physician, caregiver, to adjust a limited number of operational parameters of programmable controller 300 including starting and stopping a stimulation session. Programmable controller 300 communicates with external patient controller 400 via respective communication units, which may each comprise an inductive coil and/or RF transceiver, configured to communicate information in a bidirectional manner across a patient's skin and, optionally, to transmit power to programmable controller 300. For example, external patient controller 400 may selectively activate programmable controller 300 responsive to user input received at user interface 402 via respective telemetry (or RF) systems in controllers 300 and 400. In a preferred embodiment, a limited number of stimulation parameters may be adjusted at user interface 402 to minimize the chance of injury caused by adjustments made by non-physician users. In an alternative embodiment, external patient controller 400 also may send adjustments to stimulation parameters; e.g., pair(s) of electrodes to be used for stimulation, pulse duration, frequency of alternating current, voltage, current, period of stimulation; to programmable controller 300 responsive to user input received at user interface 402. In one embodiment, external patient controller 400 may selectively activate desired subsets of array 202 of electrodes to determine the empirically determined subset of array 202 of electrodes and to cause nonvolatile memory of programmable controller 300 to store the identity of the empirically determined subset of array 202 of electrodes and the stimulation routine sufficient to cause sexual arousal. The subset of array 202 of electrodes may include one or more electrodes within the array of electrodes. The one or more electrodes within array 202 of electrodes may be adjacent to each other or spaced apart.

External patient controller 400 may be specifically designed for use with implantable stimulation unit 200 or external patient controller 400 may be a smartphone, laptop, tablet, smartwatch, or the like programmed to communicate with implantable stimulation unit 200. Accordingly, external patient controller 400 may use an application or "app" downloaded from an app store to interface with implantable stimulation unit 200 and/or external physician controller 500, and may use cellular, 802.11 WiFi, Zigbee, and/or BLUETOOTH™ chipset(s) for communication with those devices.

External physician controller 500 is configured to control programmable controller 300 and may communicate directly with programmable controller or via external patient controller 400. In FIG. 1, external physician controller 500 is a computer having a non-transitory computer readable medium programmed with instructions that, when run on the computer, cause the computer to provide programming to programmable controller 300. External physician controller 500 may be coupled wirelessly to programmable controller 300 and/or external patient controller 400 such that external physician controller 500 may download for review data stored on programmable controller 300 and/or external patient controller 400. External physician controller 500 also may transfer programming data to programmable controller 300 to reprogram stimulation parameters programmed into programmable controller 300. For example, external physician controller 500 may be used to program and adjust parameters such as pair(s) of electrodes to be used for stimulation, pulse duration, frequency of alternating current, voltage, current, and period of stimulation. External physician controller 500 also may be configured to upload and store data retrieved from programmable controller 300 to a remote server for later access by the physician. In one embodiment, external physician controller 500 may selectively activate desired subsets of array 202 of electrodes to determine the empirically determined subset of array 202 of electrodes and to cause nonvolatile memory of programmable controller 300 to store the identity of the empirically determined subset of array 202 of electrodes and the stimulation routine sufficient to cause sexual arousal.

External physician controller 500 may be configured to selectively activate desired subsets of array 202 of electrodes by causing microprocessor of programmable controller 300 to execute a scanning protocol stored in nonvolatile memory of programmable controller 300 to determine the empirically determined subset of array 202 of electrodes and to cause nonvolatile memory of programmable controller 300 to store the identity of the empirically determined subset of array 202 of electrodes and the stimulation routine sufficient to cause sexual arousal. The scanning protocol may be configured to cause microprocessor of programmable controller 300 to supply electrical stimulation via the stimulation circuit by activating varying subsets of the array of electrodes in a predetermined manner at stimulation parameters to determine the empirically determined subset of array 202 of electrodes and optimal stimulation parameters. The stimulation parameters may be the same for each subset, varied from subset to subset, the same for select subsets and varied for other subsets, and/or varied at one or more subsets throughout the protocol. Activating varying subsets of the array of electrodes in a predetermined manner may include a first time and a second time, such that a first subset of array 202 of electrodes is activated at the first time and a second subset of array 202 of electrodes is activated at the second time in an interpulse manner. Activating in an interpulse manner may include, for example, activating the first subset of array 202 of electrodes while no other subset of array 202 of electrodes is activated at such activation time. Subsequently, when the first subset of array 202 of electrodes is no longer activated, the second subset of array 202 of electrodes is activated while no other subset of array 202 of electrodes is activated, as will be readily apparent to one skilled in the art. One or more additional subsets may be activated while other subset(s) remain inactive.

In one embodiment, external physician controller 500 is used in a post-operative (e.g., prostatectomy) period to determine the empirically determined subset of array 202 of electrodes yielding the best erectile response. The stimulation parameters are stored within memory of programmable controller 300 such that erection may be achieved using those parameters at a later time, e.g., responsive to user input at external patient controller 400.

External physician controller 500 may be specifically designed for use with implantable stimulation unit 200 or external physician controller 400 may be a smartphone, laptop, tablet, desktop computer, or the like programmed to communicate with implantable stimulation unit 200. Accordingly, external physician controller 500 may use software such as an application or "app" downloaded from an app store to interface with implantable stimulation unit 200 and/or external patient controller 400, and may use cellular, 802.11 WiFi, Zigbee, and/or BLUETOOTH™ chipset(s) for communication with those devices. External physician controller 500 may communicate directly with implantable stimulation unit 200 or with implantable stimulation unit 200 via external patient controller 400.

Figure 2A:
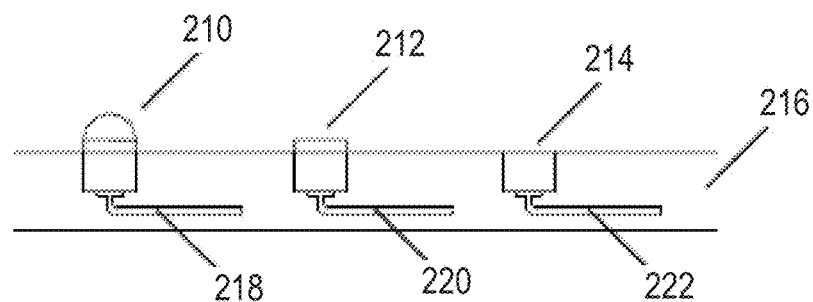
FIGS. 2A and 2B show front and perspective views, respectively, of schematic representations of possible electrode shapes within a flexible substrate.
Figure 2B:
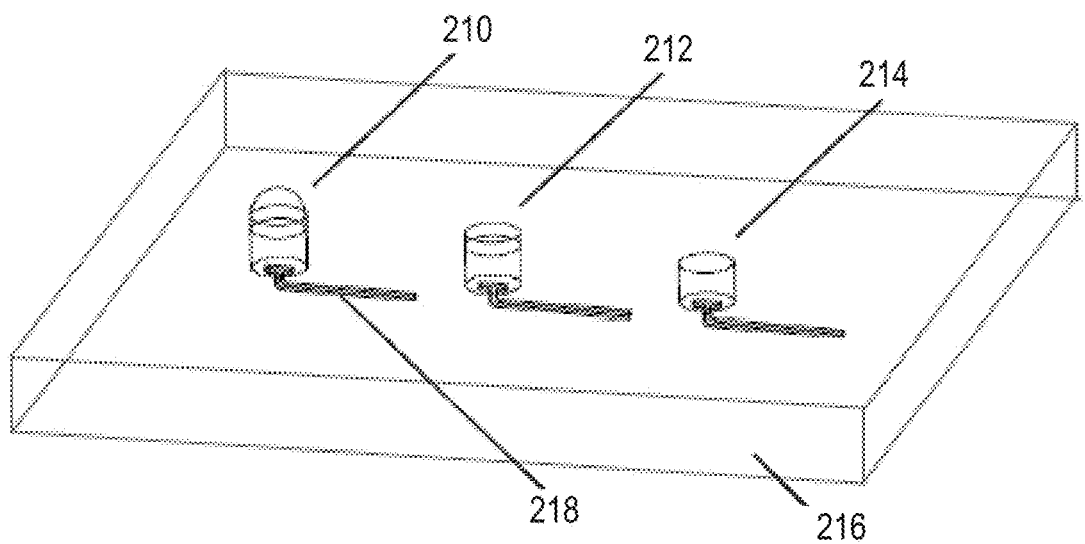

Referring now to FIGS. 2A and 2B, exemplary electrode shapes for use in implantable stimulation unit 200 are described. Electrodes 210, 212, 214 each have a tissue friendly shape configured to reduce adverse tissue reaction that may lead to fibrosis formation around the electrode. Electrode 210 has a convex portion extending from flexible substrate portion 216 and is independently coupled to the circuitry of programmable controller 300 by wire 218 of the cable. Electrode 212 has a spherical portion extending from flexible substrate portion 216 and is independently coupled to the circuitry of programmable controller 300 by wire 220 of the cable. Electrode 214 is flat and is flush with the surface of flexible substrate portion 216 and is independently coupled to the circuitry of programmable controller 300 by wire 222 of the cable. Advantageously, each of the electrode shapes does not have a sharp surface that may damage or irritate the tissue. As will also be understood by one of skill in the art, array 202 of electrodes may use one, two, or three of these electrodes shapes or other suitable tissue friendly shape(s) in array 202 of electrodes.

Figure 2C:
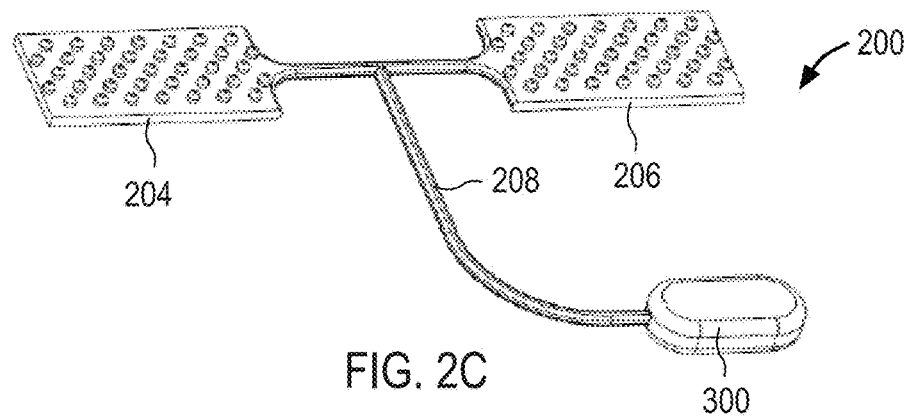
Figure 2D:
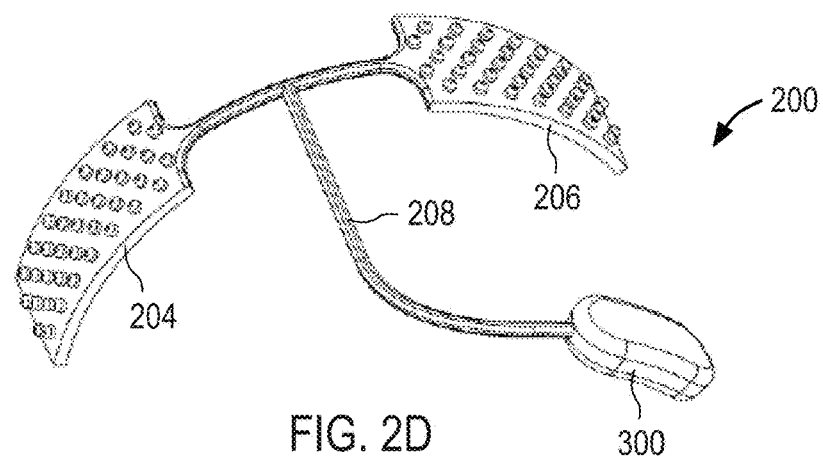
Figure 2E:
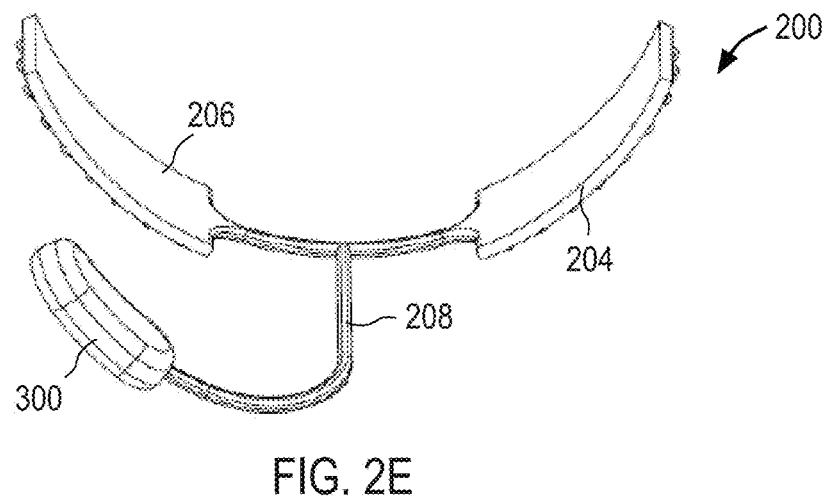

Referring now to FIGS. 2C, 2D, and 2E, exemplary implantable stimulation system 200 is shown. FIGS. 2D and 2E illustrate that first and second flexible substrates 204 and 206 are configured to bend, e.g., to an arc shape, and may be implanted (e.g., during prostatectomy surgery) on the pelvic plexus. Preferably, first and second flexible substrates 204 and 206 are conformable to an anatomical shape of a portion of the pelvic plexus. Because the pelvic plexus has a pair of nerve groups, first and second flexible substrates 204 and 206 may each cover part or the entire area of one nerve group of the pair so that at least one of the electrodes of array 202 is in optimal contact with the cavernosal nerve. For example, first flexible substrate 204 may have a length between about 1 cm to about 5 cm, about 1 cm to about 4 cm, about 1 cm to about 3 cm, about 1 cm to about 2 cm, or about 2 cm to about 4 cm. In addition, first flexible substrate 204 may have a width about 1 cm to about 3 cm, about 1 cm to about 2 cm, or about 1.5 cm to about 2.5 cm. First flexible substrate 204 may have a thickness about 0.3 mm to about 3 mm, about 0.5 mm to about 2.5 mm, about 0.5 mm to about 2 mm, about 0.5 mm to about 1.5 mm, or about 0.5 mm to about 1.0 mm. As another example, second flexible substrate 206 may have a length between about 1 cm to about 5 cm, about 1 cm to about 4 cm, about 1 cm to about 3 cm, about 1 cm to about 2 cm, or about 2 cm to about 4 cm. In addition, second flexible substrate 206 may have a width about 1 cm to about 3 cm, about 1 cm to about 2 cm, or about 1.5 cm to about 2.5 cm. Second flexible substrate 206 may have a thickness about 0.3 mm to about 3 mm, about 0.5 mm to about 2.5 mm, about 0.5 mm to about 2 mm, about 0.5 mm to about 1.5 mm, or about 0.5 mm to about 1.0 mm. First and second flexible substrates 204 and 206 may have the same dimensions or different dimensions. In addition, the distance between first flexible substrate 204 and second flexible substrate 206, when implanted, may be about 0.5 cm to about 8 cm, about 1 cm to about 7 cm, about 2 cm to about 6 cm, or about 3 cm to about 5 cm. Cable 208 is also flexible to permit a physician to manipulate programmable controller 300 to implant programmable controller 300 at a suitable location, e.g., between the skin and the pelvic bone.

Figure 3:
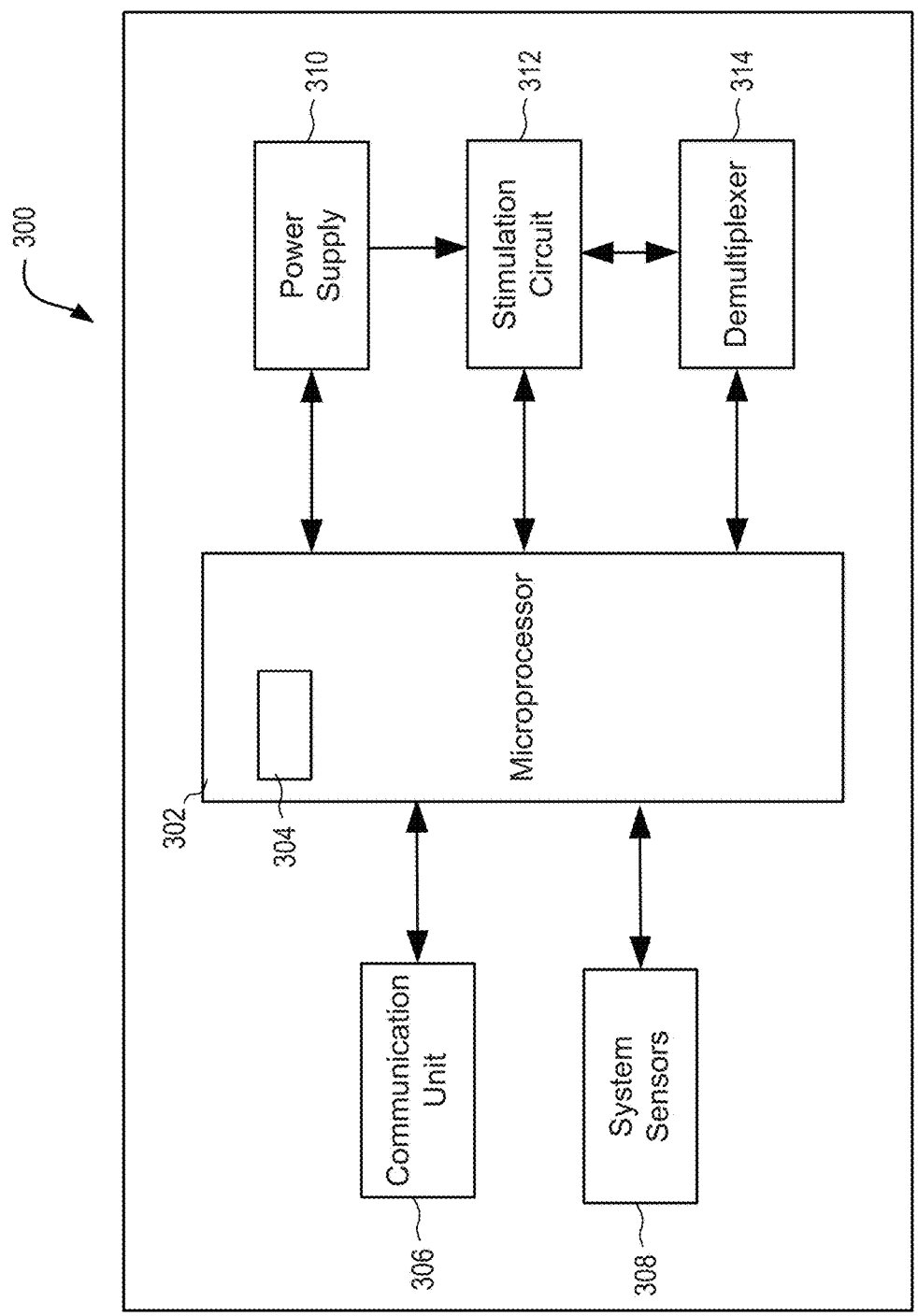
FIG. 3 shows a generalized block diagram of an exemplary programmable controller of an implantable stimulation unit of the stimulation system of FIG. 1.

With respect to FIG. 3, a generalized schematic diagram of the internal functional components of programmable controller 300 is now described. Programmable controller 300 is configured to cause the electrodes to stimulate in accordance with programming data stored in the memory of programmable controller 300. Programmable controller 300 may include microprocessor 302, nonvolatile memory 304, communication unit 306, system sensors 308, power supply 310, stimulation circuit 312, and demultiplexer 314.

Microprocessor 302 is electrically coupled to, and configured to control, the internal functional components of programmable controller 300. Microprocessor 302 may comprise a commercially available microcontroller unit including a programmable microprocessor, volatile memory, nonvolatile memory 304 such as EEPROM for storing programming and nonvolatile storage, e.g., Flash memory, for storing firmware and a log of system operational parameters and patient data. The memory of microprocessor 302 stores program instructions that, when executed by microprocessor 302, cause the processor and the functional components of programmable controller 300 to provide the functionality ascribed to them herein. Microprocessor 302 is configured to be programmable such that programming data (e.g., stimulation parameters, identity of an empirically determined subset of the array of electrodes, stimulation routines) is stored in nonvolatile memory 304 of microprocessor 302 and may be adjusted using external patient controller 400 and/or external physician controller 500.

Microprocessor 302 may be programmable to allow electrical stimulation between any chosen combination of electrodes on the array, thus providing a simple bipolar configuration. Microprocessor 302 further may be programmed with a routine to selectively activate desired subsets of the array of electrodes to determine an empirically determined subset of the array of electrodes and cause nonvolatile memory 304 to store a stimulation routine used by microprocessor 302. For example, microprocessor 302 may direct power supply 310 to send an electrical signal via stimulation circuit 312 to one or more electrodes, using demultiplexer 314, which emit electrical power. In one embodiment, the stimulation routine is used by microprocessor 302 to supply electrical stimulation via stimulation circuit 312 and the pelvic plexus to at least one cavernous nerve sufficient to cause sexual arousal, e.g., an erection. The routine may selectively activate the desired subsets automatically and/or responsive to user input at external patient controller 400 and/or external physician controller 500. The desired subset of the array (e.g., one or more stimulation electrodes) yields the best sexual arousal, e.g., erectile response, and is stored in memory. The desired subset may be determined in a direct fashion (e.g., stimulate each electrode sequentially and observe the evoked erectile response) or in an indirect/peripheral fashion (e.g., stimulate the cavernosal nerve distally, for example via external electrodes disposed on the skin of the penis, and record the signal received by the electrodes upstream). The identity of the electrode receiving the best signal is stored for later stimulation and the received electrode signals and/or the identity of the electrode receiving the best signal may be transmitted to external patient controller 400 and/or external physician controller 500.

The stimulation parameters are selected to provide sexual arousal, to promote nerve regeneration, and/or to improve nerve regeneration to treat sexual disorders such as erectile dysfunction and female sexual arousal disorder. For example, stimulation may cause and maintain an erection and may promote and/or improve nerve (e.g., nerve(s) of the pelvic plexus and/or cavernous nerve(s)) regeneration over time. As an example, pulse duration may be programmed to be between about 0.5 msec to about 10 msec, about 0.5 msec to about 5 msec, about 1 msec to about 4 sec, or about 1 msec to about 3 msec. Frequency of alternating current may be programmed to be between about 10 Hz to about 30 Hz, about 10 Hz to about 25 Hz, about 10 Hz to about 20 Hz, or about 15 Hz to about 25 Hz. Voltage may be programmed to be between about 1 V to about 15 V, about 5 V to about 10V, about 1 V to about 5 V, or about 10 V to about 15V. Current may be programmed to be between about 1 milliamp to about 100 milliamps, about 1 milliamp to about 50 milliamps, about 1 milliamp to about 20 milliamps, about 20 milliamps to about 50 milliamps, about 50 milliamps to about 100 milliamps, or about 75 milliamps to about 100 milliamps. Period of stimulation may be programmed to automatically stimulate during predetermined times or may stimulate responsive to user input, e.g., at user interface 402. For example, stimulation may be maintained during a portion or during the entire period of desired erection. For nerve regeneration, it may be preferable to stimulate at predetermined intervals over time. For example, automatic stimulation may occur hourly, once a day, twice a day, three times a day, four times a day, every other day, every three days, or weekly for a period of 10 min to 2 hours, 10 min to 1 hour, 10 min to 30 min, 10 min to 20 min, or 1 hour to 2 hours.

Preferably, stimulation for nerve regeneration occurs using oscillating current or low-frequency electrical stimulation.

Microprocessor 302 is coupled to communication unit 306 having circuitry configured to communicate external patient controller 400 and/or external physician controller 500. Communication unit 306 permits transmission of stimulation commands, and optionally power, between programmable controller 300 and external patient controller 400 such that programmable controller 300 may be powered, programmed, and/or controlled by external patient controller 400. For example, microprocessor 302 may start or stop a stimulation session or to conduct an assessment to determine optimal subset of the array of electrodes responsive to stimulation commands received from a corresponding communication unit (e.g., an inductive unit having a telemetry system and coil and/or a RF unit having a transceiver and antenna) of external patient controller 400. Communication unit 306 further permits transmission of programming data, and optionally power, between programmable controller 300 and external physician controller 500 such that programmable controller 300 may be powered, programmed, and/or controlled by external physician controller 500. For example, microprocessor 302 may direct changes to pair(s) of electrodes to be used for stimulation, pulse duration, frequency of alternating current, voltage, current, and/or period of stimulation and may conduct an assessment to determine optimal subset of the array of electrodes responsive to programming data received from a corresponding communication unit (e.g., an inductive unit having a telemetry system and coil and/or a RF unit having a transceiver and antenna) of external physician controller 500.

Communication unit 306 may include a telemetry system electrically coupled to an inductive coil. The technology for telemetry systems and coils is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer. Alternatively, the coil may be used to transmit power only, and separate radio frequency transmitters may be provided in programmable controller 300, external patient controller 400, and/or external physician controller 500 for establishing bidirectional or unidirectional data communication.

Communication unit 306 also may include (with or without the telemetry system and coil) a communications circuit employing a transceiver coupled to an antenna (which may be inside or external to the hermetic housing). The transceiver preferably comprises a radio frequency (RF) transceiver and is configured for bi-directional communications via the antenna with a similar transceiver circuit disposed in external patient controller 400 and/or external physician controller 500. For example, the transceiver may receive stimulation commands from external patient controller 400 and programming data from external physician controller 500. Microprocessor 302 may direct changes to pair(s) of electrodes to be used for stimulation, pulse duration, frequency of alternating current, voltage, current, and/or period of stimulation, may start or stop a stimulation session, and/or may conduct an assessment to determine optimal subset of the array of electrodes, responsive to programming data and/or stimulation commands received from a corresponding transceiver and antenna of external patient controller 400 and/or external physician controller 500 via the antenna and the transceiver of communication unit 306. The transceiver also may include a low power mode of operation, such that it periodically awakens to listen for incoming messages and responds only to those messages including the unique device identifier assigned to that programmable controller. In addition, the transceiver may employ an encryption routine to ensure that messages sent from, or received by, programmable controller 300 cannot be intercepted or forged. Communication unit 306 may include a wireless chipset; e.g., WiFi, BLUETOOTH™, cellular, Zigbee, or the like; thereby enabling programmable controller 300 to communicate wirelessly with external patient controller 400 and/or external physician controller 500.

System sensors 308 may comprise one or more sensors that monitor operation of the systems of programmable controller 300, and log data relating to system operation as well as system faults, which may be stored in a log for later readout using external physician controller 500. Microprocessor 302 may be configured to receive a sensor signal from system sensors 308 and to adjust the stimulation parameters based on the sensor signal. Sensors 308 may include, for example, a humidity sensor to measure moisture within the housing of programmable controller 300, which may provide information relating to the state of the electronic components, and/or a temperature sensor, e.g., for measuring battery temperature during charging to ensure safe operation of the battery. Data from the system sensors may be logged by microprocessor 302 and stored in nonvolatile memory 304 for later transmission to external physician controller 500.

Power supply 310 powers the electrical components of programmable controller 300, and may comprise a primary cell or battery, a secondary (rechargeable) cell or battery or a combination of both. Alternatively, power supply 310 may not include a cell or battery, but instead comprise a capacitor that stores energy transmitted through the skin via a Transcutaneous Energy Transmission System (TETs), e.g., by inductive coupling. In a preferred embodiment, power supply 310 comprises a lithium ion battery.

Stimulation circuit 312 is configured to send pulses, using energy supplied from power supply 310, to the electrodes of the array such that the selected electrode(s) supply electrical stimulation at the desired parameters.

Microprocessor 302 further may be coupled to demultiplexer 314 so that any subset of electrodes of the electrode array may be selectably coupled to stimulation circuit 312. In this way, an appropriate electrode set may be chosen from the entire selection of electrodes implanted in the patient's body to achieve a desired therapeutic effect. Demultiplexer 314 preferably operates at high speed, thereby allowing successive stimulation pulses to be applied to different electrode combinations.

Figure 4:
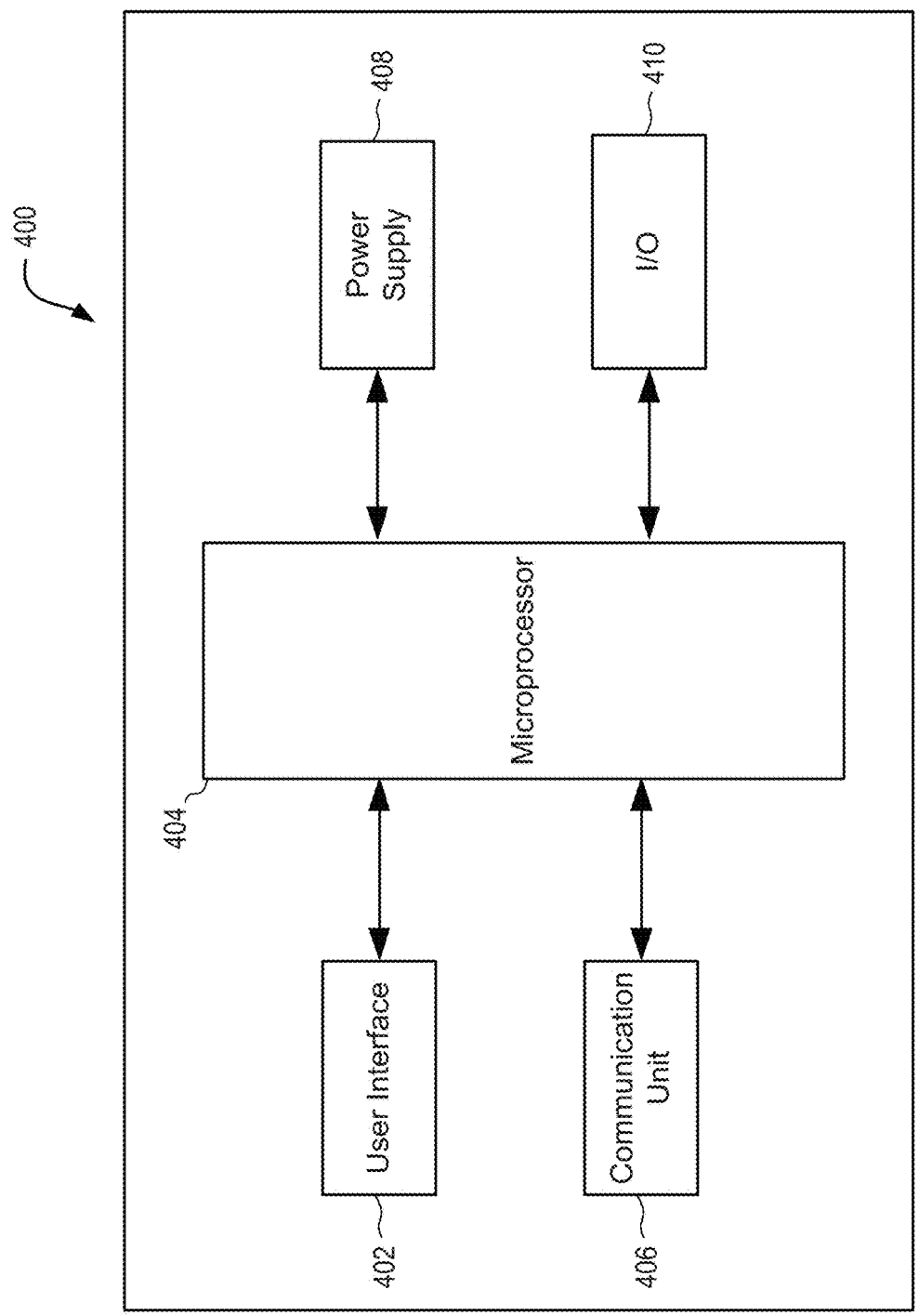
FIG. 4 shows a generalized block diagram of an exemplary external patient controller of the stimulation system of FIG. 1.

With respect to FIG. 4, a generalized schematic diagram of the internal functional components of external patient controller 400 is now described. External patient controller 400 may include user interface 402, programmable microprocessor 404, communication unit 406, power supply 408, and input and output circuitry (I/O) 410. As explained above, external physician controller 400 may be specifically designed for use with implantable stimulation unit 200 or may be a multipurpose smartphone, laptop, tablet, smartwatch, or the like programmed to communicate with implantable stimulation unit 200 and/or external patient controller 500. In the latter case, user interface 402, programmable microprocessor 404, communication unit 406, power supply 408, and I/O 410 may be hardware previously installed on the smartphone, laptop, tablet, smartwatch, or the like.

Microprocessor 404 is electrically coupled to, and configured to control, the internal functional components of external patient controller 400. Microprocessor 404 may comprise a commercially available microcontroller unit including a programmable microprocessor, volatile memory, nonvolatile memory such as EEPROM for storing programming and nonvolatile storage, e.g., Flash memory, for storing firmware and a log of system operational parameters and patient data. The memory of microprocessor 404 may store program instructions that, when executed by the processor of microprocessor 404, cause the processor and the functional components of external patient controller 400 to provide the functionality ascribed to them herein. Microprocessor 404 is configured to be programmable. For example, microprocessor 404 may store and adjust stimulation parameters; e.g., pair(s) of electrodes to be used for stimulation, pulse duration, frequency of alternating current, voltage, current, and/or period of stimulation; responsive to user input received at user interface 402 and/or at an external physician controller 500 and send stimulation commands and programming data to programmable controller 300 via communication unit 406.

Microprocessor 404 may be coupled to communication unit 406, which is configured to communicate with programmable controller 300 and external physician controller 500. Communication unit 406 may include an inductive unit having a telemetry system and coil and/or a RF unit having a transceiver and antenna with a wireless chipset; e.g., WiFi, BLUETOOTH™, cellular, Zigbee, or the like; thereby enabling external patient controller 400 to communicate wirelessly with programmable controller 300 and/or external physician controller 500 and to optionally supply power to programmable controller 300.

User interface 402 is configured to receive user input and to display information to the user. User interface 402 may include buttons, LEDs, a display, a touch screen, a keypad, a microphone, a speaker, a trackball, or the like for receiving user input and/or displaying information to the user. For example, user interface 402 may display current stimulation parameters and permit a user to adjust the stimulation parameters. In a preferred embodiment, a limited number of stimulation parameters may be adjusted at user interface 402 to minimize the chance of injury caused by adjustments made by non-physician users. For example, user interface 402 may only permit a user to start or stop a stimulation session using the empirically determined subset of array 202 of electrodes and the stimulation routine sufficient to cause sexual arousal.

Power supply 408 powers the electrical components of external patient controller 400, and may comprise a primary cell or battery, a secondary (rechargeable) cell or battery or a combination of both. Alternatively, power supply 408 may be a port to allow external patient controller 400 to be plugged into a conventional wall socket for powering components.

Input and output circuitry (I/O) 410 may include ports for data communication such as wired communication with a computer and/or ports for receiving removable memory, e.g., SD card, upon which program instructions or data related to external patient controller 400 use may be stored.

Figure 5:
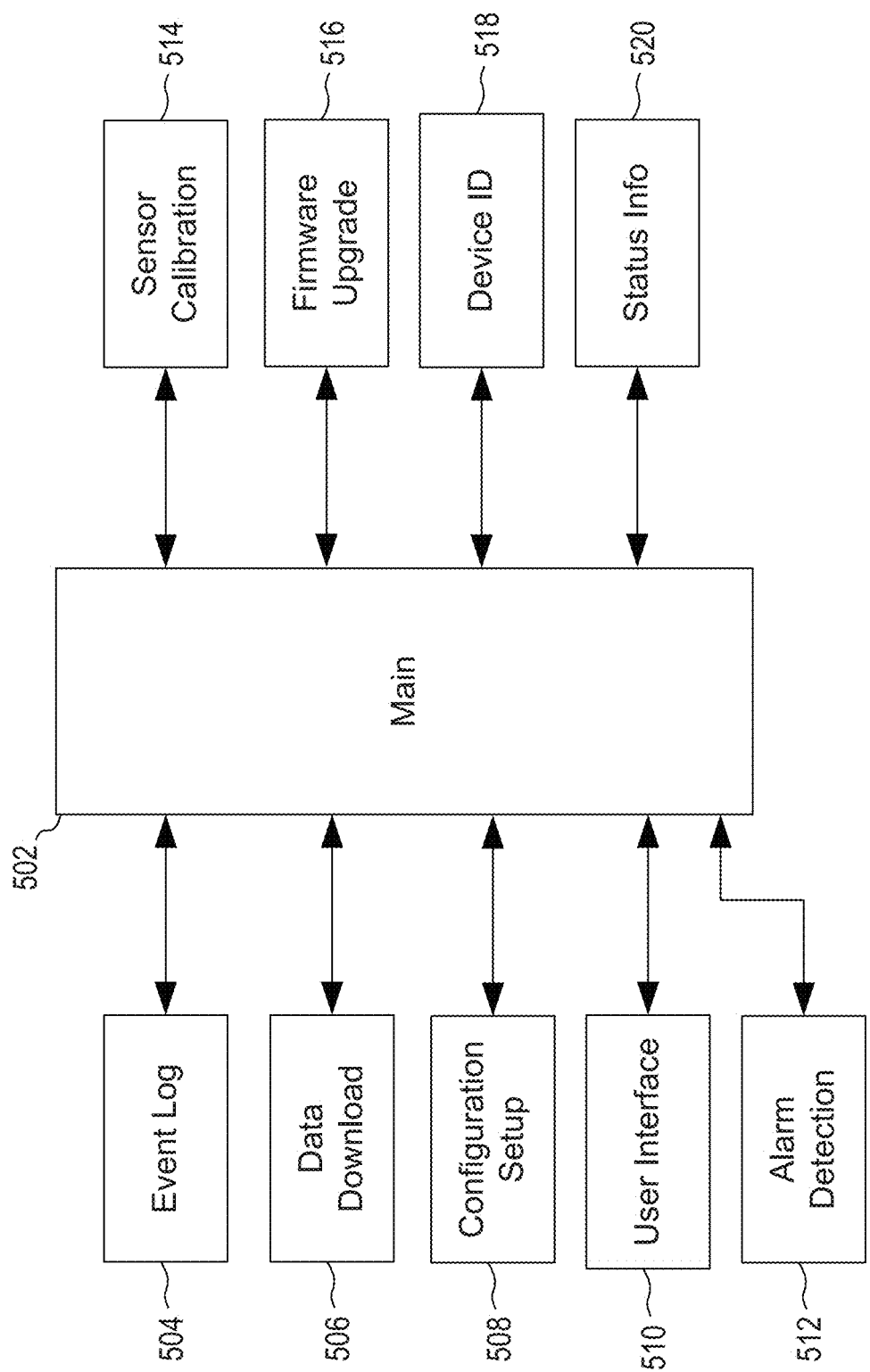
FIG. 5 is a block diagram of the functional components of an exemplary software-based programming system configured to run on the external physician controller of the stimulation system of FIG. 1.

Referring now to FIG. 5, the software implemented on external physician controller 500 is now described. The software comprises a number of functional blocks, schematically depicted in FIG. 5, including main block 502, event logging block 504, data download block 506, configuration setup block 508, user interface block 510, alarm detection block 512, sensor calibration block 514, firmware upgrade block 516, device identifier block 518, and status information block 520. The software preferably is written in C++ and employs an object oriented format. In one preferred embodiment, the software is configured to run on top of a Microsoft Windows® (a registered trademark of Microsoft Corporation, Redmond, Wash.) or Unix-based operating system, such as are conventionally employed on desktop and laptop computers. As discussed above, the computer may include a transceiver, an antenna, and a wireless card; e.g., conforming to the IEEE 802.11 standard, cellular, BLUETOOTH™, Zigbee, or the like; thereby enabling programmable controller 300 and/or external patient controller 400 to communicate wirelessly with external physician controller 500.

Main block 502 preferably includes a main software routine that executes on the physician's computer, and controls overall operation of the other functional blocks. Main block 502 enables the physician to download event data and alarm information stored on programmable controller 300 and/or external patient controller 400, to his office computer, and also permits external physician controller 500 to directly control operation of programmable controller 300. Main block 502 also enables the physician to upload firmware updates and configuration data to programmable controller 300.

Event Log block 504 is a record of operational data downloaded from programmable controller 300 and may include, for example, treatment session start and stop times, current stimulation parameters, stimulation parameters from previous treatment sessions, sensor data, battery current, battery voltage, battery status, and the like. The event log also may include the occurrence of events, such as alarms or other abnormal conditions.

Data Download block 506 is a routine that commands programmable controller 300, to transfer data to external physician controller 500 for download after programmable controller 300 is coupled to external physician controller 500. Data Download block 506 may initiate, either automatically or at the instigation of the physician via user interface block 510, downloading of data stored in the event log.

Configuration Setup block 508 is a routine that configures the parameters stored within programmable controller 300 that control operation of programmable controller 300. The interval timing parameters may determine, e.g., how long the processor remains in sleep mode prior to being awakened to listen for radio communications or to control programmable controller 300 operation. The interval timing parameters may control, for example, the duration of a stimulation session. Interval timing settings transmitted to programmable controller 300 also may determine when and how often event data is written to the memory in microprocessor 302. In an embodiment in which external physician controller 500 is also configured to transfer data to external patient controller 400, external physician controller 500 also may be used to configure timing parameters used by the firmware executed by microprocessor 404 of external patient controller 400. Block 508 also may be used by the physician to configure parameters stored within the memory of microprocessor 302 relating to limit values on operation of microprocessor 302. These values may include times when programmable controller 300 may and may not operate, etc.

Block 508 also may configure parameters stored within the memory of microprocessor 302 relating to control of operation of programmable controller 300. These values may include stimulation parameters.

User interface block 510 handles display of information retrieved from programmable controller 300 and/or external patient controller 400 and data download block 506, and presents that information in an intuitive, easily understood format for physician review. Such information may include status of programmable controller 300, treatment session start and stop times, current stimulation parameters, stimulation parameters from previous treatment sessions, sensor data, battery status, and the like. User interface block 510 also generates user interface screens that permit the physician to input information to configure the session timing, stimulation parameters, requests to determine the subset of the array of electrodes optimal for sexual arousal, etc.

Alarm detection block 512 may include a routine for evaluating the data retrieved from programmable controller 300 and flagging abnormal conditions for the physician's attention. For example, alarm detection block 512 may flag when a parameter measured by system sensors 308 is above or below a predetermined threshold.

Sensor calibration block 514 may include a routines for testing or measuring drift, of system sensors 308 employed in programmable controller 300, e.g., due to aging or change in humidity. Block 514 may then compute offset values for correcting measured data from the sensors, and transmit that information to programmable controller 300 for storage in the nonvolatile memory of microprocessor 302.

Firmware upgrade block 516 may comprise a routine for checking the version numbers of the controller firmware installed on programmable controller 300 and/or external patient controller 400 and identify whether upgraded firmware exists. If so, the routine may notify the physician and permit the physician to download revised firmware to programmable controller 300 and/or external patient controller 400, in nonvolatile memory.

Device identifier block 518 may include a unique identifier for programmable controller 300 that is stored in the nonvolatile memory of microprocessor 302 and a routine for reading that data when external physician controller 500 is coupled to programmable controller 300. The device identifier also may be used by programmable controller 300 to confirm that wireless communications received from external patient controller 400 and/or external physician controller 500 are intended for that specific programmable controller. Likewise, this information is employed by external patient controller 400 and/or external physician controller 500 to determine whether a received message was generated by the programmable controller associated with that system. Finally, the device identifier information may be employed by external physician controller 500 to confirm that external patient controller 400 and programmable controller 300 constitute a matched set.

Status information block 520 comprises a routine for interrogating programmable controller 300 to retrieve current status data from programmable controller 300. Such information may include, for example, battery status, stimulation parameters, the date and time on the internal clocks of treatment sessions, version control information for the firmware and hardware currently in use, and sensor data.

Figure 6:
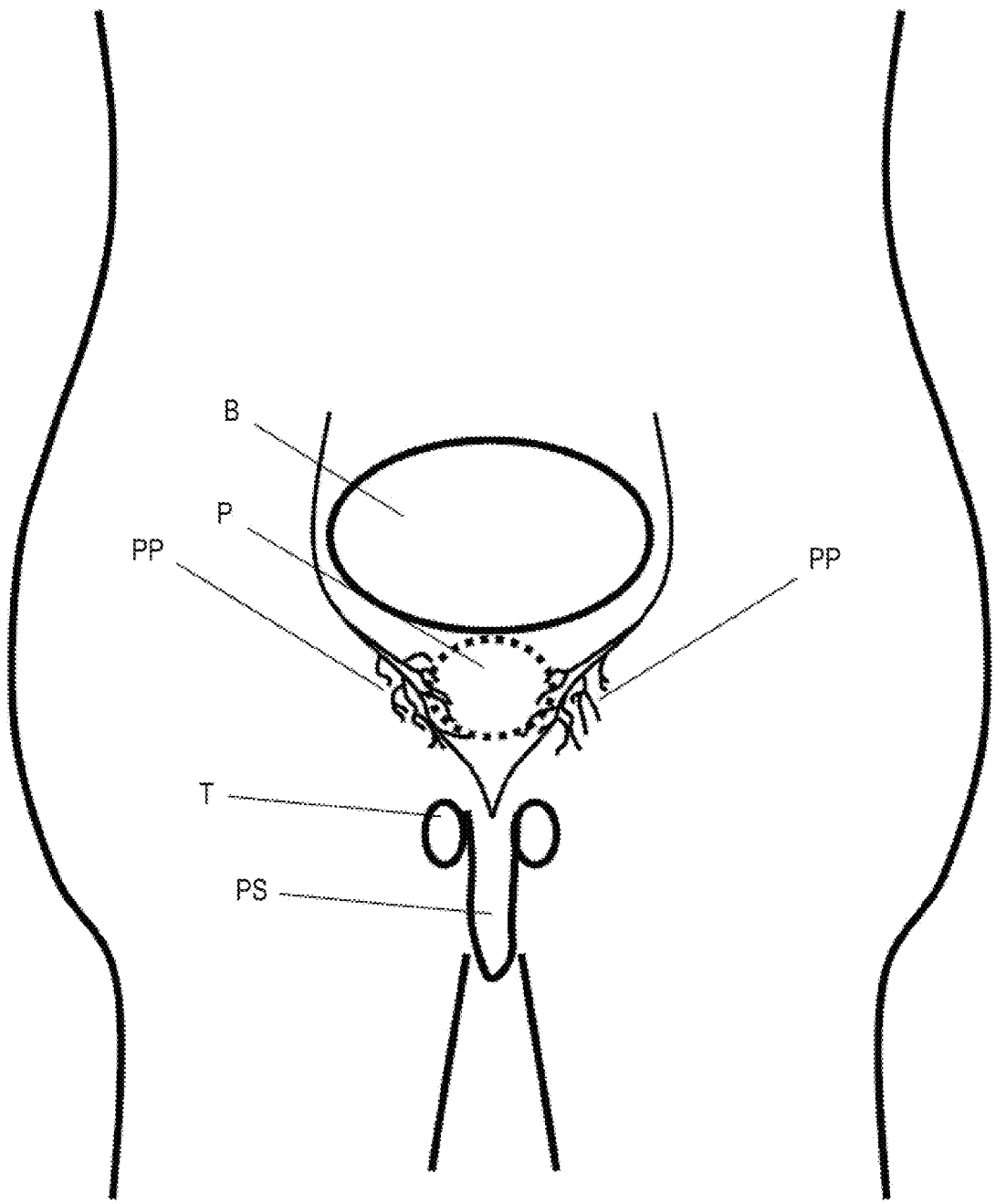
FIG. 6 is a schematic representation of the local anatomy.
Figure 7:
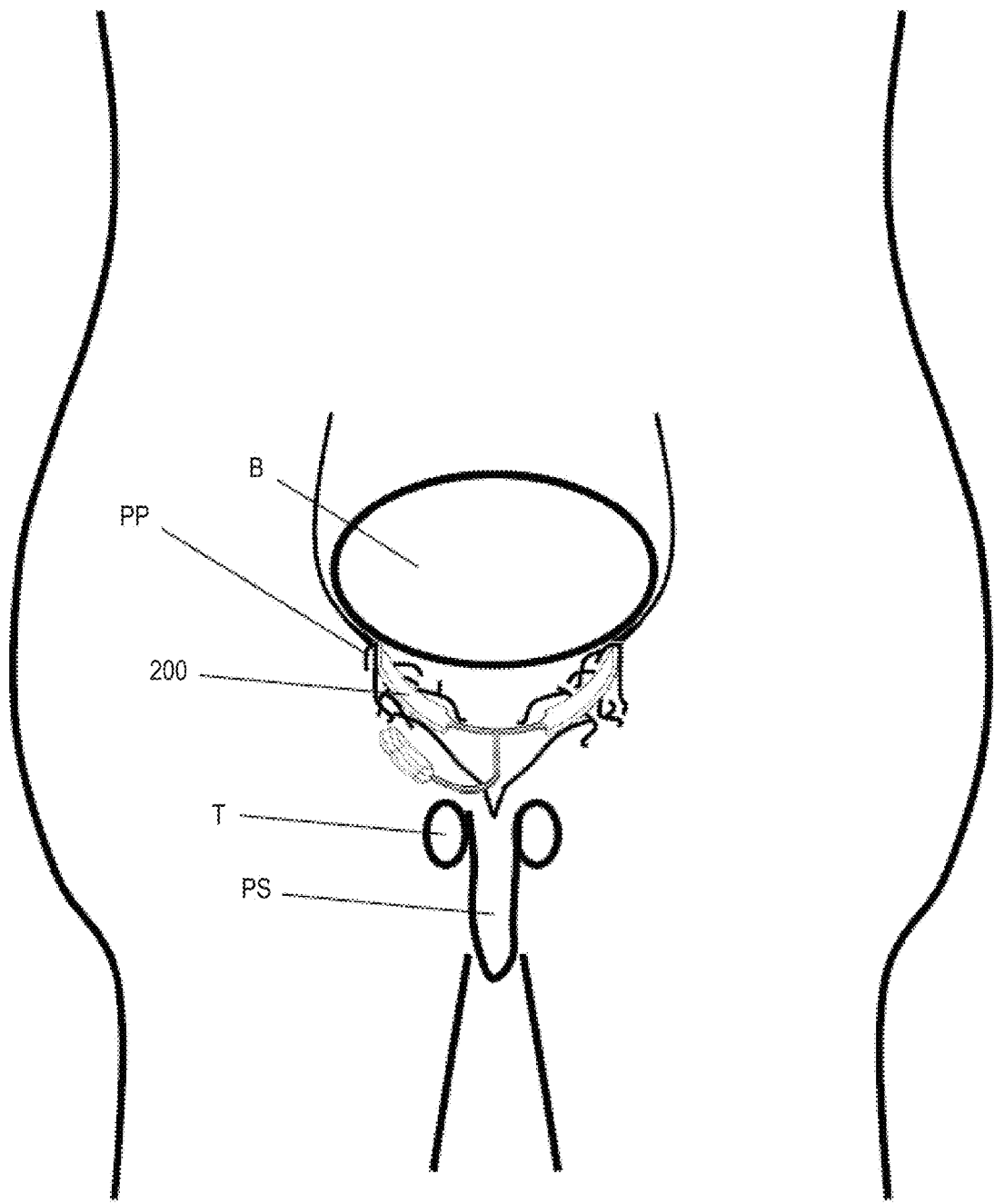
FIG. 7 illustrates positioning of the implantable stimulation unit on the neuronal pelvic plexus.

Referring now to FIGS. 6 and 7, an exemplary method for implanting an implantable stimulation unit is described. FIG. 6 is a schematic representation of the local anatomy showing the bladder B, prostate P, a pair of nerve groups known as the pelvic plexus PP, the testis T, and the penis PS. In this example, implantable stimulation unit 200 is implanted following prostatectomy, although the disclosure is not limited thereto. Preferably, implantable stimulation unit 200 is inserted in the patient via the incision used to remove the prostate P. Implantable stimulation unit 200 may be implanted using a robotic-guided surgery system. Insertion may be visualized using, for example, fluoroscopy, acoustic, anatomic, or CT guidance. The incision may be in the lower abdomen or perineum. In one embodiment, one or more trocars are inserted in the incision and implantable stimulation unit 200; including first flexible substrate 204, second flexible substrate 206, cable 208, and programmable controller 300; is sized and shaped to be implanted through the respective lumen(s) of the one or more trocars. As is shown in FIG. 7, the first and second flexible substrates are configured to bend, e.g., to an arc shape, and implanted on the pelvic plexus PP permitting molding, apposition, and adaptation to the local anatomy by the substrates. Preferably, the first and second flexible substrates are conformable to an anatomical shape of a portion of the pelvic plexus PP. Because the pelvic plexus PP has a pair of nerve groups, the first and second flexible substrates may each cover part or the entire area of one nerve group of the pair so that at least one of the electrodes of the array is in optimal contact with the cavernosal nerve. The first and second flexible substrates may be anchored to tissue, e.g., via one or more sutures and/or biocompatible glue. The cable of implantable stimulation unit 200 is also flexible to permit a physician to manipulate the programmable controller such that the programmable controller is implanted at a suitable location, e.g., subderma and/or subderma between the skin and the pelvic bone. The programmable controller may be anchored to tissue, e.g., via one or more sutures and/or biocompatible glue. The incisions may then be closed. Advantageously, the implantation procedure is fast, thereby avoiding long periods of surgery. In addition, optimal placement of the electrodes relative to the cavernosal nerve does not need to be determined during surgery and may be determined post-surgery. Electrical stimulation system 100 provides a painless, safe, easier, non-traumatic, and more effective alternative for the treatment of sexual disorders such as ED.

Figure 8:
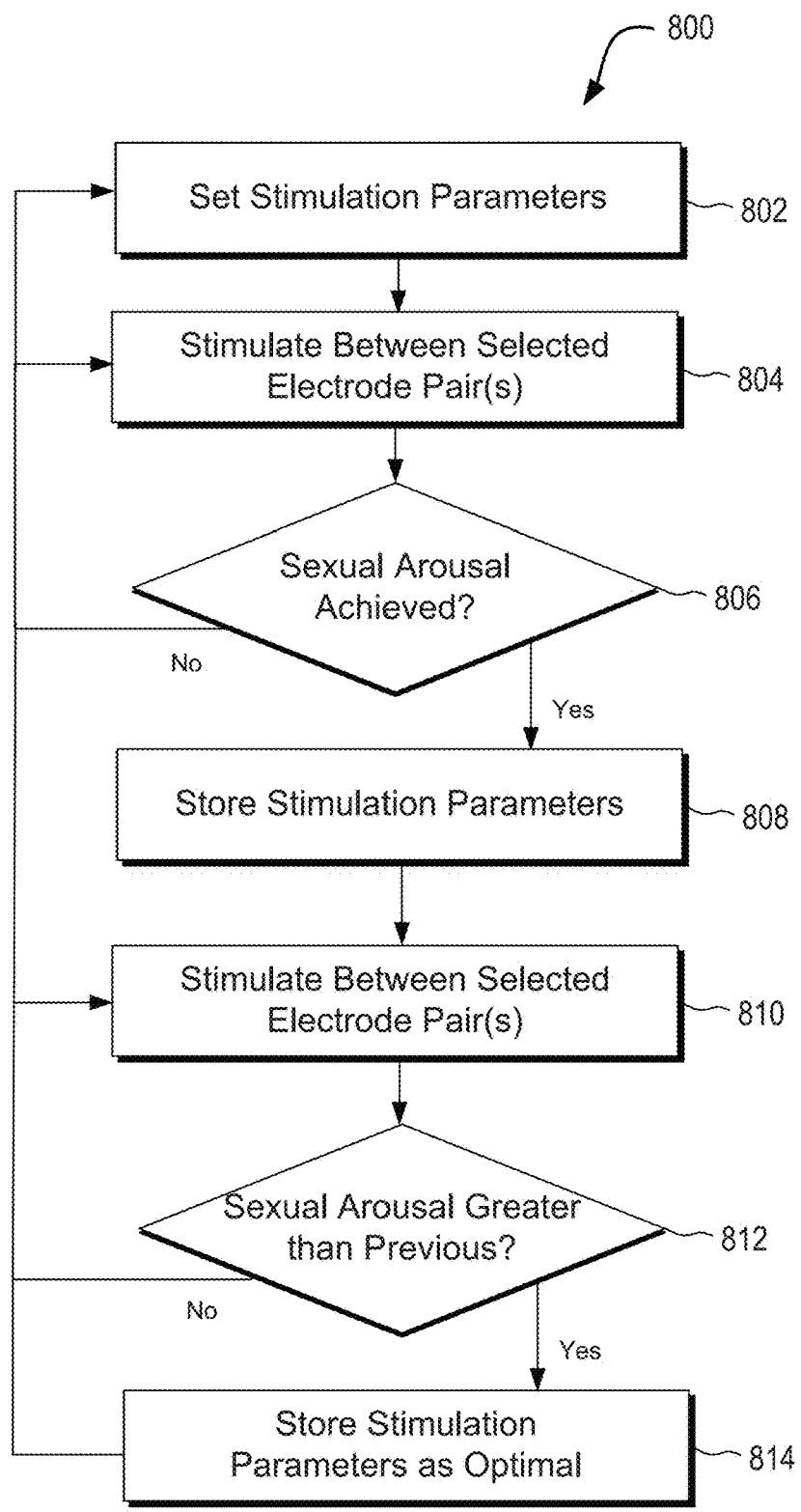
FIG. 8 shows an exemplary method for empirically determining a subset of the array of electrodes for stimulation to cause optimal sexual arousal.

In FIG. 8, an exemplary method for empirically determining a subset of the array of electrodes positioned to supply electrical stimulation to at least one cavernous nerve via the pelvic plexus to cause sexual arousal, e.g., an erection, preferably post-implantation, is shown. In method 800, at 802, stimulation parameters are set which may include the pair(s) of electrode in the array to be used, pulse duration, frequency of alternating current, voltage, current, and period of stimulation. Stimulation parameters may be set at external patient controller 400, but are preferably set at external physician controller 500. At 804, electrical stimulation is supplied to tissue, e.g., pelvic plexus, between the selected electrode pair(s) of the array at the set stimulation parameters. The selected electrode pair(s) of the array at the set stimulation parameters may be selected by a physician via the external physician controller and/or determined as a result of the scanning protocol described above. At 806, it is observed whether sexual arousal, e.g., an erection, is achieved. If not, stimulation parameters may be reset for the selected electrode pair(s) or different electrode pair(s) may be selected for stimulation with the same parameters or at adjusted parameters. If sexual arousal is achieved, the stimulation parameters, including the electrode pair(s), are stored in memory at programmable controller 300, external patient controller 400, and/or physician controller 500. Optionally, even after sexual arousal is achieved, further stimulation may be conducted at the electrode pair(s) using adjusted stimulation parameters or further different electrode pair(s) may be selected for stimulation with the same parameters or at adjusted parameters, at 810, to determine if greater sexual arousal can be achieved, at 812. If not, stimulation, at 810, may be repeated with different configurations or the testing may end and the parameters stored at 808 may be used. If greater sexual arousal is achieved, the stimulation parameters, including the electrode pair(s), are stored in memory at programmable controller 300, external patient controller 400, and/or physician controller 500 as the optimal parameters and the previously stored parameters at 808 may be overwritten. Optionally, even after greater sexual arousal is achieved, further stimulation may be conducted at the electrode pair(s) using adjusted stimulation parameters or further different electrode pair(s) may be selected for stimulation with the same parameters or at adjusted parameters, at 810, to determine if even greater sexual arousal can be achieved, at 812. Once the user is satisfied that the optimal parameters have been determined, either because all electrode pairings in the array were tested or because suitable sexual arousal was achieved, the optimal parameters are stored. In this manner, a stimulation routine at the optimal parameters may be initiated by patient external controller 400 and/or external physician controller 500 at a later time; e.g., minutes, hours, days, months, years later; to cause sexual arousal, e.g., an erection.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A method of treating a sexual disorder, the method comprising:
    placing an array of electrodes adjacent a prostate or where a native prostate was located prior to prostatectomy, the array of electrodes disposed on at least one flat flexible substrate;
    selectively activating subsets of the array of electrodes to empirically determine an identity of a subset of the array of electrodes comprising the at least one electrode;
    storing the identity of the empirically determined subset of the array of electrodes; and
    supplying electrical stimulation via the empirically determined subset of the array of electrodes to stimulate a pelvic plexus and thereby at least one cavernous nerve to cause an erection.

2. The method of claim 1, wherein the at least one flat flexible substrate is sized and shaped to abut at least a portion of the pelvic plexus and configured to bend to conform to an anatomical shape of the portion of the pelvic plexus.

3. The method of claim 1, wherein electrodes of the array of electrodes comprise a plurality of rows and a plurality of columns disposed on the at least one flat flexible substrate and each electrode is individually selectable.

4. The method of claim 1, wherein the at one least flat flexible substrate comprises a first flat flexible substrate configured to conform to a first half of the pelvic plexus and a second flat flexible substrate configured to conform to a second half of the pelvic plexus.

5. The method of claim 4, wherein a first portion of the array of electrodes is disposed on the first flat flexible substrate and a second portion of the array of electrodes is disposed on the second flat flexible substrate, wherein supplying the electrical stimulation via the empirically determined subset of the array of electrodes comprises supplying the electrical stimulation to one or more electrodes of the first portion and one or more electrodes of the second portion at a same time in a bilateral stimulation manner.

6. The method of claim 1, wherein supplying the electrical stimulation via the empirically determined subset of the array of electrodes comprises initiating a stimulation routine executed by an implantable processor operatively coupled to the array of electrodes.

7. The method of claim 6, wherein the stimulation routine is initiated responsive to a command wirelessly transmitted by an external patient controller to the implantable processor.

8. The method of claim 6, wherein the stimulation routine specifies one or more of pulse duration, frequency of alternating current, voltage, current, or period of stimulation sufficient to cause the erection.

9. The method of claim 6, further comprising adjusting the stimulation routine by adjusting stimulation parameters at the implantable processor responsive to one or more commands wirelessly received.

10. The method of claim 9, further comprising wirelessly sending the one or more commands by an external physician controller or an external patient controller after supplying the electrical stimulation.

11. The method of claim 1, wherein selectively activating subsets of the array of electrodes is executed via an external physician controller operatively coupled to the array of electrodes.

12. The method of claim 1, wherein selectively activating subsets of the array of electrodes comprises executing a scanning protocol via an implantable processor operatively coupled to the array of electrodes.

13. The method of claim 12, wherein executing the scanning protocol comprises activating varying subsets of the array of electrodes in a predetermined manner to determine the empirically determined subset of the array of electrodes.

14. The method of claim 13, wherein activating the varying subsets of the array of electrodes in the predetermined manner comprises activating a first subset of the array of electrodes at a first time and activating a second subset of the array of electrodes at a second time in an interpulse manner.

15. The method of claim 13, wherein activating the varying subsets of the array of electrodes in the predetermined manner comprises activating a first subset of the array of electrodes at a first time and activating either the first subset of the array of electrodes at different stimulation parameters or a second subset of the array of electrodes at a same or different stimulation parameters.

16. The method of claim 1, further comprising anchoring the array of electrodes to maintain the array of electrodes in contact with the pelvic plexus.

17. The method of claim 16, wherein anchoring the array of electrodes comprises anchoring the array of electrodes with sutures or biocompatible glue.

18. The method of claim 1, further comprising:
    receiving an electrical signal emitted by one or more external electrodes disposed on a skin of a penis of the patient via at least one electrode of the array of electrodes; and
    recording and storing information indicative of the received electrical signal.

\* \* \* \* \*